(12) United States Patent
Chang et al.

(10) Patent No.: US 8,597,647 B1
(45) Date of Patent: Dec. 3, 2013

(54) HUMANIZED ANTI-IL-20 ANTIBODY AND USES THEREOF

(75) Inventors: Ming-Shi Chang, Tainan (TW); Naoya Tsurushita, Palo Alto, CA (US); Shankar Kumar, Pleasanton, CA (US)

(73) Assignee: National Cheng Kung University, Tainan (TW)

( * ) Notice: Subject to any disclaimer, the term of this patent is extended or adjusted under 35 U.S.C. 154(b) by 0 days.

(21) Appl. No.: 13/477,476

(22) Filed: May 22, 2012

(51) Int. Cl.
*A61K 39/395* (2006.01)
*A61K 39/00* (2006.01)
*C07K 16/00* (2006.01)
*C12P 21/08* (2006.01)

(52) U.S. Cl.
USPC .............. 424/145.1; 424/133.1; 424/141.1; 530/387.1; 530/387.3; 530/388.1; 530/388.23

(58) Field of Classification Search
None
See application file for complete search history.

(56) References Cited

U.S. PATENT DOCUMENTS

| | | | |
|---|---|---|---|
| 7,179,892 B2 * | 2/2007 | Basi et al. ................. | 530/387.3 |
| 7,318,923 B2 * | 1/2008 | Tsurushita et al. ........ | 424/133.1 |
| 7,435,800 B2 | 10/2008 | Chang | |
| 7,611,705 B2 * | 11/2009 | Chang ....................... | 424/141.1 |
| 7,700,751 B2 * | 4/2010 | Basi et al. .................. | 536/23.1 |
| 7,786,274 B2 | 8/2010 | Chang | |
| 7,837,994 B2 | 11/2010 | Chang | |
| 8,012,478 B2 | 9/2011 | Chang | |
| 2008/0233115 A1 | 9/2008 | Xu et al. | |
| 2009/0048432 A1 | 2/2009 | Chang | |
| 2011/0305698 A1 | 12/2011 | Chang | |
| 2011/0305699 A1 | 12/2011 | Chang | |

OTHER PUBLICATIONS

Rudikoff et al Proc Natl Acad Sci USA 79: 1979, 1982.*
Barrios et al 2004. J Molecular Recognition 17: 332-338.*
MacCallum et al Mol. Biol 262: 732-745, 1996.*
Queen et al., A humanized antibody that binds to the interleukin 2 receptor. Proc Natl Acad Sci USA. Dec. 1989;86(24):10029-33.

* cited by examiner

*Primary Examiner* — Shulamith H Shafer
(74) *Attorney, Agent, or Firm* — Wolf, Greenfield & Sacks, P.C.

(57) ABSTRACT

The present disclosure provides humanized antibodies specific to human interleukin 20 (IL-20) and uses thereof in treating diseases associated with the IL-20 signaling pathway, e.g., osteoporosis, inflammatory disease (e.g., rheumatoid arthritis), cancer, stroke, and renal failure.

15 Claims, 1 Drawing Sheet

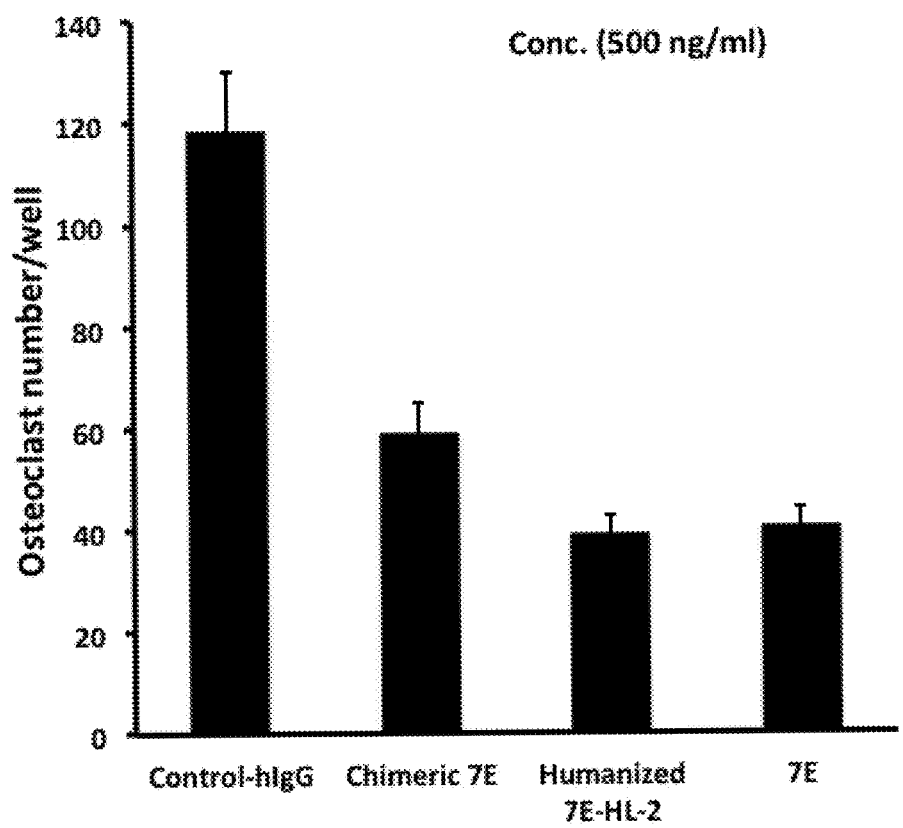

US 8,597,647 B1

HUMANIZED ANTI-IL-20 ANTIBODY AND USES THEREOF

BACKGROUND OF THE INVENTION

Interleukin 20 (IL-20), a pleiotropic inflammatory cytokine, is a member of the IL-10 family, which includes IL-10, IL-19, IL-20, IL-22, IL-24, and IL-26. IL-20 is expressed in monocytes, epithelial cells, and endothelial cells. It acts on multiple types of cells via activating a heterodimer receptor complex of either IL-20R1/IL-20R2 or IL-22R1/IL-20R2. IL-20 has been found to be involved in various diseases, such as psoriasis, rheumatoid arthritis, atherosclerosis, ischemic stroke, osteoporosis, and renal failure. Certain anti-IL-20 antibodies have been reported to possess therapeutic effects in treating IL-20 associated diseases, e.g., osteoporosis and rheumatoid arthritis. U.S. Pat. Nos. 7,435,800, 7,611,705, 7,786,274, 7,837,994, 8,012,478; and US Patent Publications 20110305699 and 20090048432.

Monoclonal antibodies derived from non-human species are routinely used in biochemistry, molecular biology, and medical research. In addition, they are attractive therapeutic agents because of their high target specificity and effector functionality. However, one problem associated with the use of non-human antibodies as therapeutic agents is their immunogenicity, which substantially reduces the in vivo effectiveness of such antibodies. One approach to reduce immunogenicity is humanization, i.e., modifying non-human antibodies to increase their similarity to naturally-occurring human antibodies.

SUMMARY OF THE INVENTION

The present disclosure is based on the development of two humanized anti-IL-20 antibodies, which exhibited unexpectedly high affinity to IL-20 (i.e., $K_d<3.6\times10^{-9}$) and therapeutic effects in treating IL-20-associated diseases, e.g., osteoporosis. Accordingly, one aspect of the present disclosure features a humanized antibody that binds IL-20, particularly human IL-20. This antibody comprises a heavy chain variable region ($V_H$), which comprises an amino acid sequence at least 90% (e.g., 95%, 96%, 97%, 98%, or 99%) identical to SEQ ID NO:1 or SEQ ID NO:3, and a light chain variable region ($V_L$), which comprises an amino acid sequence at least 90% (e.g., 95%, 96%, 97%, 98%, or 99%) identical to SEQ ID NO:5 or SEQ ID NO:7. In one example, the humanized anti-IL-20 antibody comprises a $V_H$ chain that comprises SEQ ID NO:1 or SEQ ID NO:3 and a $V_L$ chain that comprises SEQ ID NO:5, SEQ ID NO:7, or SEQ ID NO:15.

The humanized anti-IL-20 antibody described above can be a full-length antibody (e.g., an IgG molecule), an antigen-binding fragment thereof (e.g., Fab), or a single-chain antibody.

In another aspect, the present disclosure provides an isolated nucleic acid comprising a nucleotide sequence encoding (i) a $V_H$ chain, which comprises an amino acid sequence at least 90% (e.g., 95%, 96%, 97%, 98%, or 99%) identical to SEQ ID NO:1 or SEQ ID NO:3, (ii) a $V_L$ chain, which comprises an amino acid sequence at least 90% (e.g., 95%, 96%, 97%, 98%, or 99%) identical to SEQ ID NO:5 or SEQ ID NO:7, or (iii) both. In one example, the nucleic acid comprises (i) a nucleotide sequence of SEQ ID NO:2 or SEQ ID NO:4, (ii) a nucleotide sequence of SEQ ID NO:6 or SEQ ID NO:8, or (iii) both. Also described herein are vectors, which comprise the just-described nucleic acids, and host cells which comprise such vectors. In one example, the vectors are expression vectors and the nucleic acids coding for the $V_H$ and/or $V_L$ chains are in operable linkage to a suitable promoter. Each of the $V_H$ and $V_L$ coding sequences can be in operably linkage with an individual promoter. Alternatively, both of the $V_H$ and $V_L$ genes can be under the control of a common promoter.

In yet another aspect, the present disclosure provides methods for treating diseases associated with an IL-20-mediated signaling pathway, comprising administering to a patient in need thereof an effective amount of the humanized anti-IL-20 antibody described herein, either the antibody per se, or a plasmid(s) for expressing such. Diseases associated with the IL-20 mediated signaling pathway include, but are not limited to osteoporosis, rheumatoid arthritis, cancer, stroke, or renal failure. In one example, the disease is osteoporosis, which can be caused by an inflammatory disease (e.g., rheumatoid arthritis), estrogen deficiency (e.g., menopause), androgen deficiency (e.g., andropause), or cancer-induced osteolysis. In another example, the disease is cancer, such as breast cancer, prostate cancer, colon cancer, lung cancer, renal cell carcinoma, giant cell tumor of bone, oral cancer, esophagus cancer, or multiple myeloma.

Also within the scope of this disclosure are (i) a pharmaceutical composition comprising the humanized anti-IL-20 antibody described herein or a nucleic acid encoding the $V_H$ chain of the antibody, the $V_L$ chain of the antibody, or both, and a pharmaceutically acceptable carrier; (ii) the just-noted pharmaceutical composition for use in treating a disease associated with an IL-20-mediated signaling pathway, such as those described above, and (iii) the use of the humanized anti-IL-20 antibody or its encoding nucleic acid(s)/vectors in the manufacture of a medicament for the treatment of any of the above described diseases.

The details of one or more embodiments of the invention are set forth in the description below. Other features or advantages of the present invention will be apparent from the following drawings and detailed description of several embodiments, and also from the appended claims.

BRIEF DESCRIPTION OF THE DRAWINGS

The drawings are first described.

FIG. 1 is a chart showing the inhibitory effects of a humanized anti-IL-20 antibody on osteoclast differentiation, as compared with the effects of the parent mouse monoclonal antibody mAb 7E and a chimeric antibody derived therefrom. Bone marrow-derived hematopoetic stem cells were cultured with MCSF and RANKL to drive osteoclast differentiation. Addition of an anti-IL-20 antibody as noted above to the culture at a concentration of 500 ng/ml inhibited 50% of osteoclast differentiation.

BRIEF DESCRIPTION OF THE SEQUENCES

SEQ ID NO:1 is the amino acid sequence of the precursor $V_H$ chain variable region of exemplary humanized anti-IL-20 antibodies HL1 and HL2.

SEQ ID NO:2 is the nucleotide sequence encoding the amino acid sequence of SEQ ID NO:1.

SEQ ID NO:3 is the amino acid sequence of the mature $V_H$ chain variable region (which lacks the signal peptide) of the exemplary humanized anti-IL-20 antibodies HL1 and HL2.

SEQ ID NO:4 is the nucleotide sequence encoding the amino acid sequence of SEQ ID NO:3.

SEQ ID NO:5 is the amino acid sequence of the precursor $V_L$ chain variable region of exemplary humanized anti-IL-20 antibody HL2.

SEQ ID NO:6 is the nucleotide sequence encoding the amino acid sequence of SEQ ID NO:5.

SEQ ID NO:7 is the amino acid sequence of the mature $V_L$ chain variable region (which lacks the signal peptide) of exemplary humanized anti-IL-20 antibody HL2.

SEQ ID NO:8 is the nucleotide sequence encoding the amino acid sequence of SEQ ID NO:7.

SEQ ID NO:9 is the amino acid sequence of the precursor $V_H$ chain variable region of monoclonal antibody 7E.

SEQ ID NO:10 is the amino acid sequence of the precursor $V_L$ chain variable region of monoclonal antibody 7E.

SEQ ID NO:11 is the amino acid sequence of the mature $V_H$ chain variable region (which lacks the signal peptide) of monoclonal antibody 7E.

SEQ ID NO:12 is the amino acid sequence of human germline antibody $V_H$ segment J606.4.82.

SEQ ID NO:13 is the amino acid sequence of the framework regions in human antibody L06102 $V_H$ chain (mature form).

SEQ ID NO:14 is the amino acid sequence of the mature $V_L$ chain variable region (which lacks the signal peptide) of monoclonal antibody 7E.

SEQ ID NO:15 is the amino acid sequence of the mature $V_L$ chain variable region (which lacks the signal peptide) of exemplary humanized anti-IL-20 antibody HL1.

SEQ ID NO:16 is the amino acid sequence of human germline antibody bd2 $V_L$ segment.

SEQ ID NO:17 is the amino acid sequence of the framework regions in human antibody BG758592 $V_L$ chain (mature form).

DETAILED DESCRIPTION OF THE INVENTION

Described herein are humanized anti-IL-20 antibodies and their uses in treating diseases associated with an IL-20-mediated signaling pathway.

Humanized Anti-IL-20 Antibodies

The humanized anti-IL-20 antibodies described herein were designed based on a parent mouse monoclonal antibody 7E, which is described in U.S. Pat. Nos. 7,435,800 and 7,786,274, and also in Example 1 below.

A "humanized antibody" can be an antibody derived from modifying a non-human antibody to replace certain antibody fragments (e.g., framework regions) with those from a human antibody so as to reduce immunogenicity in humans. The humanized antibody described herein can be in any antibody form. In some embodiments, they are intact immunoglobulin molecules (full-length antibodies), including IgG, IgA, IgD, IgE, and IgM. In other embodiments, the humanized antibodies are antigen binding fragments thereof, e.g., Fab, F(ab')$_2$, and Fv. In some instances, they also can be single-chain antibodies or bi-specific antibodies.

Humanized antibodies can be designed as follows. First, the variable regions of $V_H$ and $V_L$ of a parent non-human antibody are subjected to three-dimensional molecular modeling analysis following methods known in the art. See, e.g., Queen et al., *Proc. Natl. Acad. Sci. USA*, 86:10029-10033 (1989). Next, framework amino acid residues predicted to be important for the formation of the correct CDR structures are identified using the same molecular modeling analysis. In parallel, human $V_H$ and $V_L$ chains having amino acid sequences that are homologous to those of the parent non-human antibody are identified from any antibody gene database using the parent $V_H$ and $V_L$ sequences as search queries. Human $V_H$ and $V_L$ acceptor genes are then selected.

The CDR regions within the selected human acceptor genes can be replaced with the CDR regions from the parent non-human antibody or functional variants thereof. When necessary, residues within the framework regions of the parent chain that are predicted to be important in interacting with the CDR regions (see above description) can be used to substitute for the corresponding residues in the human acceptor genes.

Provided below is an example of the humanized anti-IL-20 antibodies described herein:

Amino Acid Sequence and Encoding Nucleotide Sequence of the $V_H$ Chain of Humanized Anti-IL-20 Antibodies HL1 and HL2:

```
ATG TAC TTG GGA CTG AAC TAT GTT TTC ATC GTT TTT CTC CTG AAT
 M   Y   L   G   L   N   Y   V   F   I   V   F   L   L   N

GGT GTC CAG AGT GAA GTG CAG CTT GTG GAG TCT GGA GGA GGC TTG GTG CAG CCT GGA
 G   V   Q   S   E   V   Q   L   V   E   S   G   G   G   L   V   Q   P   G

GGA TCC CTG AAA CTC TCT TGT GCT GCC TCT GGA TTC ACT TTT AGT GAC GCC TGG ATG
 G   S   L   K   L   S   C   A   A   S   G   F   T   F   S   D   A   W   M

GAC TGG GTC CGC CAG GCT TCC GGG AAG GGG CTT GAG TGG ATT GCT GAA ATT AGA AGC
 D   W   V   R   Q   A   S   G   K   G   L   E   W   I   A   E   I   R   S

AAA GCT AAT AAT TAT GCA ACA TAC TTT GCT GAG TCT GTG AAA GGG AGG TTC ACC ATC
 K   A   N   N   Y   A   T   Y   F   A   E   S   V   K   G   R   F   T   I

TCA AGA GAT GAT TCC AAA AAC ACC GCC TAC CTG CAA ATG AAC AGC TTA AAA ACC GAG
 S   R   D   D   S   K   N   T   A   Y   L   Q   M   N   S   L   K   T   E

GAC ACT GCC GTT TAT TAC TGT ACC AAG TTA TCA CTG CGT TAC TGG TTC TTC GAT GTC
 D   T   A   V   Y   Y   C   T   K   L   S   L   R   Y   W   F   F   D   V

TGG GGC CAG GGG ACC CTG GTC ACC GTC TCC TCA (SEQ ID NO: 2)
 W   G   Q   G   T   L   V   T   V   S   S   (SEQ ID NO: 1)
```

The underlined region refers to the signal peptide and the boldfaced/italic regions are the CDRs. SEQ ID NOs: 3 and 4 represent the mature $V_H$ amino acid sequence (lacking the signal peptide) and its encoding nucleotide sequence, respectively.

Amino Acid Sequence and Encoding Nucleotide Sequence of the $V_L$ Chain (VL2) of a Humanized Anti-IL-20 Antibody HL2:

```
ATG ATG AGT CCT GCC CAG TTC CTG TTT CTG TTG GTG CTC TGG ATT
 M   M   S   P   A   Q   F   L   F   L   L   V   L   W   I

CGG GAA ACC AAC GGT GAT ATC GTG ATG ACC CAG ACT CCA CTC TCT TTG TCC GTT
 R   E   T   N   G   D   I   V   M   T   Q   T   P   L   S   L   S   V

ACC CCT GGA CAA CCA GCC TCC ATC TCT TGC AAG TCA AGT CAG AGC CTC TTG GAT
 T   P   G   Q   P   A   S   I   S   C   K   S   S   Q   S   L   L   D

AGT GAT GGA AAG ACA TAT TTG AAT TGG TTG TTA CAG AAG CCA GGC CAG TCT CCA
 S   D   G   K   T   Y   L   N   W   L   L   Q   K   P   G   Q   S   P

CAG CAC CTC ATC TAT CTG GTG TCT AAA CTG GAC TCT GGA GTC CCT GAC AGG TTC
 Q   H   L   I   Y   L   V   S   K   L   D   S   G   V   P   D   R   F

AGT GGC AGT GGA TCA GGG ACC GAT TTC ACA CTG AAA ATC AGC AGA GTG GAG GCT
 S   G   S   G   S   G   T   D   F   T   L   K   I   S   R   V   E   A

GAG GAT GTT GGA GGT TAT TAT TGC TGG CAA AGT ACA CAT TTT CCC TGG ACC TTC
 E   D   V   G   V   Y   Y   C   W   Q   S   T   H   F   P   W   T   F

GGT GGA GGC ACC AAG GTG GAA ATC AAA   (SEQ ID NO: 6)
 G   G   G   T   K   V   E   I   K    (SEQ ID NO: 5)
```

The underlined region refers to the signal peptide and the boldfaced/italic regions are the CDRs. SEQ ID NOs: 7 and 8 represent the mature $V_L$ amino acid sequence (lacking the signal peptide) and its encoding nucleotide sequence, respectively.

Also described herein are functional variants of the above disclosed exemplary humanized anti-IL-20 antibodies HL1 and HL2. Such functional variants can comprise a $V_H$ chain that comprises an amino acid sequence at least 85% (e.g., 90%, 92%, 94%, 95%, 96%, 97%, 98%, or 99%) identical to that of the $V_H$ of HL1 and HL2 (precursor or mature form; SEQ ID NO:1 and SEQ ID NO:3, respectively) and a $V_L$ chain that has an amino acid sequence at least 85% (e.g., 90%, 92%, 94%, 95%, 96%, 97%, 98%, or 99%) identical to that of the $V_L$ of HL2 (precursor or mature form; SEQ ID NO:5 and SEQ ID NO:7, respectively). These variants are capable of binding to an IL-20 molecule, particularly a human IL-20 molecule. In some examples, the variants possess similar antigen-binding affinity relative to the exemplary humanized antibody described above (e.g., having a $K_d < 4 \times 10^{-9}$).

The "percent identity" of two amino acid sequences is determined using the algorithm of Karlin and Altschul *Proc. Natl. Acad. Sci. USA* 87:2264-68, 1990, modified as in Karlin and Altschul *Proc. Natl. Acad. Sci. USA* 90:5873-77, 1993. Such an algorithm is incorporated into the NBLAST and XBLAST programs (version 2.0) of Altschul, et al. *J. Mol. Biol.* 215:403-10, 1990. BLAST protein searches can be performed with the XBLAST program, score=50, wordlength=3 to obtain amino acid sequences homologous to the protein molecules of interest. Where gaps exist between two sequences, Gapped BLAST can be utilized as described in Altschul et al., *Nucleic Acids Res.* 25(17):3389-3402, 1997. When utilizing BLAST and Gapped BLAST programs, the default parameters of the respective programs (e.g., XBLAST and NBLAST) can be used.

In some embodiments, the functional variants described above contains one or more mutations (e.g., conservative substitutions) in the FRs of either the $V_H$ or the $V_L$ as compared to those in SEQ ID NO:3 or SEQ ID NO:7. Preferably, such mutations do not occur at residues which are predicted to interact with one or more of the CDRs (see Example 1 below). As known in the art, mutations within the FR regions are unlikely to affect the antigen-binding activity of the antibody.

In other embodiments, the functional variants described herein contain one or more mutations (e.g., 1, 2, or 3) within one or more of the CDR regions. Preferably, such functional variants retain the same regions/residues responsible for antigen-binding as the parent, such as the same specificity-determining residues inside the CDRs.

Any of the humanized anti-IL-20 antibodies can be prepared via conventional methodology, e.g., recombination technology. See, e.g., Green et al. (1994) Nature Genetics 7, 13; and U.S. Pat. Nos. 5,545,806 and 5,569,825.

When a full-length antibody is desired, coding sequences of any of the humanized $V_H$ and $V_L$ chains described herein can be linked to the coding sequences of the Fc region of a human immunoglobulin and the resultant gene encoding a full-length antibody heavy and light chains can be expressed and assembled in a suitable host cell, e.g., a plant cell, a mammalian cell, a yeast cell, or an insect cell.

Antigen-binding fragments can be prepared via routine methods. For example, F(ab')$_2$ fragments can be produced by pepsin digestion of an full-length antibody molecule, and Fab fragments that can be generated by reducing the disulfide bridges of F(ab')$_2$ fragments. Alternatively, such fragments can be prepared via recombinant technology by expressing the heavy and light chain fragments in suitable host cells (e.g., *E. coli*, yeast, mammalian, plant, or insect cells) and have them assembled to form the desired antigen-binding fragments either in vivo or in vitro.

A single-chain antibody can be prepared via recombinant technology by linking a nucleotide sequence coding for a heavy chain variable region and a nucleotide sequence coding for a light chain variable region. Preferably, a flexible linker is incorporated between the two variable regions.

A humanized anti-IL-20 antibody produced as described above can be examined to determine their properties, such as antigen-binding activity and biological function, following routine methods, e.g., those described in Example 2 below.

Also disclosed herein are nucleic acids encoding any of the humanized anti-IL-20 antibodies described herein, vectors such as expression vectors comprising these nucleic acids, and host cells comprising the vectors. In one example, both the heavy and light chain coding sequences are included in one expression vector. In another example, each of the heavy and light chains of the antibody is cloned in to an individual vector. In the latter case, the expression vectors encoding the heavy and light chains can be co-transfected into one host cell for expression of both chains, which can be assembled to form intact antibodies either in vivo or in vitro. Alternatively, the expression vector encoding the heavy chain and that encoding the light chain can be introduced into different host cells for expression each of the heavy and light chains, which can then be purified and assembled to form intact antibodies in vitro.

Uses of Humanized Anti-IL-20 Antibody

The humanized anti-IL-20 antibodies described herein can be used as therapeutic agents and diagnostic agents, as well as research tools in biochemistry, molecular biology, and medical researches.

Accordingly, disclosed herein are methods for treating a disease associated with the IL-20-mediated cell signaling (e.g., an inflammatory disease such as rheumatoid arthritis, osteoporosis, cancer, stroke, and renal failure) comprising administering to a subject in need of the treatment an effective amount of any of the humanized anti-IL-20 antibody described herein.

The humanized anti-IL-20 antibodies described herein can be used for treating diseases associated with an IL-20-mediated signaling pathway, such as an inflammatory disease (e.g., rheumatoid arthritis), stroke, osteoporosis, and cancer (e.g., breast cancer, prostate cancer, colon cancer, lung cancer, renal cell carcinoma, giant cell tumor of bone, oral cancer, esophagus cancer, or multiple myeloma).

In some embodiments, the method described herein aims at treating osteoporosis and alleviating bone loss. A human subject who needs this treatment can be a patient suffering from or is suspected of having osteoporosis, which is a disease characterized by low bone mass and loss of bone tissue, resulting in weak and fragile bones. Osteoporosis to be treated by the method described herein can be induced by various factors, e.g., low levels of estrogen (e.g., caused by menopause), inadequate up take of calcium and vitamin D, inflammation (e.g., rheumatoid arthritis), cancer-induced osteolysis, and low levels of androgen (e.g., caused by andropause).

In one example, a subject (e.g., a human patient) who needs the just-noted treatment is a post-menopausal woman or a post-andropausal man. In another example, the patient is a rheumatoid arthritis patient who suppers from or is suspected of having bone erosion. In yet another example, the patient suffers from or is suspected of having osteolysis induced by cancer, such as breast cancer, prostate cancer, liver cancer, colon cancer, multiple myeloma, or lung cancer.

As used herein, the term "treating" refers to the application or administration of a composition including one or more active agents to a subject, who has a disorder/disease associated with the signaling pathway mediated by IL-20 (e.g., those described herein), a symptom of the disease/disorder, or a predisposition toward the disease/disorder, with the purpose to cure, heal, alleviate, relieve, alter, remedy, ameliorate, improve, or affect the disease/disorder, the symptom of the disease/disorder, or the predisposition toward the disease/disorder.

"An effective amount" as used herein refers to the amount of each active agent required to confer therapeutic effect on the subject, either alone or in combination with one or more other active agents. Effective amounts vary, as recognized by those skilled in the art, depending on the particular condition being treated, the severity of the condition, the individual patient parameters including age, physical condition, size, gender and weight, the duration of the treatment, the nature of concurrent therapy (if any), the specific route of administration and like factors within the knowledge and expertise of the health practitioner. These factors are well known to those of ordinary skill in the art and can be addressed with no more than routine experimentation. It is generally preferred that a maximum dose of the individual components or combinations thereof be used, that is, the highest safe dose according to sound medical judgment. It will be understood by those of ordinary skill in the art, however, that a patient may insist upon a lower dose or tolerable dose for medical reasons, psychological reasons or for virtually any other reasons.

In some embodiments, the amount of the humanized anti-IL-20 antibody described herein is effective in suppressing inflammation (e.g., reducing the level of inflammation by at least 20%, 30%, 50%, 80%, 100%, 200%, 400%, or 500% as compared to a blank control). In other embodiments, the amount of the humanized anti-IL-20 antibody described herein is effective in inhibiting bone loss (e.g., reducing the level of bone loss by at least 20%, 30%, 50%, 80%, 100%, 200%, 400%, or 500% as compared to a blank control).

To practice a treatment disclosed herein, any of the humanized anti-IL-20 antibody or the encoding nucleic acid can be mixed with a pharmaceutically acceptable carrier to form a pharmaceutical composition for administration to a subject in need of the treatment. A pharmaceutically acceptable carrier is compatible with the active ingredient(s) in the composition (and preferably, capable of stabilizing it) and not deleterious to the subject to be treated. For example, solubilizing agents such as cyclodextrins, which form more soluble complexes with a humanized anti-IL-20 antibody as described herein, or a nucleic acid encoding such, or more solubilizing agents, can be utilized as pharmaceutical carriers for delivery of the agonist/antagonist. Examples of other carriers include colloidal silicon dioxide, magnesium stearate, sodium lauryl sulfate, and D&C Yellow #10. See, e.g., Remington's Pharmaceutical Sciences, Edition 16, Mack Publishing Co., Easton, Pa. (1980); and Goodman and Gilman's "The Pharmacological Basis of Therapeutics", Tenth Edition, Gilman, J. Hardman and L. Limbird, eds., McGraw-Hill Press, 155-173, 2001.

The pharmaceutical compositions, formulated for therapeutic uses, may be prepared for storage by mixing an agent having the desired degree of purity with optional pharmaceutically acceptable carriers, excipients or stabilizers (Remington's Pharmaceutical Sciences 16th edition, Osol, A. Ed. (1980)), in the form of lyophilized formulations or aqueous solutions. Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG).

To treating a target disease, an effective amount of the pharmaceutical composition noted above can be administered to a subject (e.g., a human) in need of the treatment via a suitable route. A human subject who needs the treatment may be a human patient having, at risk for, or suspected of having a disorder associated with the signaling pathway mediated by IL-20. Such a patient can be identified by routine medical examination.

If necessary, the pharmaceutical composition described herein, containing a humanized anti-IL-20 antibody or its encoding nucleic acid(s), can be co-administered with a second therapeutic agent. The selection of the second therapeutic agent depends on the type of the disease to be treated. For example, if the target disease is an inflammatory disease such as rheumatoid arthritis, the second agent can be a TNFα antagonist, which can be an etanercept polypeptide, infliximab, or adalimumab. In another example, if the target disease is a cancer, the second agent can be an anti-cancer agent (e.g., Tamoxifen, Taxol, Erlotinib, Dexasone, and Herceptin).

When the pharmaceutical composition described here is co-used with a second therapeutic agent, a sub-therapeutic dosage of either the composition or of the second agent, or a sub-therapeutic dosage of both, can be used in the treatment of a subject having, or at risk of developing a disease or disorder associated with the cell signaling mediated by IL-20. A "sub-therapeutic dose" as used herein refers to a dosage, which is less than that dosage which would produce a therapeutic result in the subject if administered in the absence of the other agent or agents. Thus, the sub-therapeutic dose of an agent is one which would not produce the desired therapeutic result in the subject in the absence of the administration of the agents of the invention. Therapeutic doses of many agents that are in clinical use are well known in the field of medicine, and additional therapeutic doses can be determined by those of skill without undue experimentation. Therapeutic dosages have been extensively described in references such as Remington's Pharmaceutical Sciences, 18th ed., 1990; as well as many other medical references relied upon by the medical profession as guidance for the treatment of diseases and disorders.

Conventional methods, known to those of ordinary skill in the art of medicine, can be used to administer the pharmaceutical composition to the subject, depending upon the type of diseases to be treated or the site of the disease. This composition can also be administered via other conventional routes, e.g., administered orally, parenterally, by inhalation spray, topically, rectally, nasally, buccally, vaginally or via an implanted reservoir. The term "parenteral" as used herein includes subcutaneous, intracutaneous, intravenous, intramuscular, intraarticular, intraarterial, intrasynovial, intrasternal, intrathecal, intralesional, and intracranial injection or infusion techniques. In addition, it can be administered to the subject via injectable depot routes of administration such as using 1-, 3-, or 6-month depot injectable or biodegradable materials and methods.

Injectable compositions may contain various carriers such as vegetable oils, dimethylactamide, dimethyformamide, ethyl lactate, ethyl carbonate, isopropyl myristate, ethanol, and polyols (glycerol, propylene glycol, liquid polyethylene glycol, and the like). For intravenous injection, water soluble antibodies can be administered by the drip method, whereby a pharmaceutical formulation containing the antibody and a physiologically acceptable excipients is infused. Physiologically acceptable excipients may include, for example, 5% dextrose, 0.9% saline, Ringer's solution or other suitable excipients. Intramuscular preparations, e.g., a sterile formulation of a suitable soluble salt form of the antibody, can be dissolved and administered in a pharmaceutical excipient such as Water-for-Injection, 0.9% saline, or 5% glucose solution.

When a nucleic acid(s) encoding a humanized anti-IL-20 antibody as described herein is used as the therapeutic agent, the nucleic acid(s) or a vector(s) expressing the antibody can be delivered to a subject by methods, such as that described in Akhtar et al., 1992, Trends Cell Bio. 2, 139. For example, it can be introduced into cells using liposomes, hydrogels, cyclodextrins, biodegradable nanocapsules, or bioadhesive microspheres. Alternatively, the nucleic acid or vector can be locally delivered by direct injection or by use of an infusion pump. Other approaches include employing various transport and carrier systems, for example through the use of conjugates and biodegradable polymers.

To facilitate delivery, any of the humanized anti-IL-20 antibody or its encoding nucleic acids can be conjugated with a chaperon agent. As used herein, "conjugated" means two entities are associated, preferably with sufficient affinity that the therapeutic benefit of the association between the two entities is realized. Conjugated includes covalent or noncovalent bonding as well as other forms of association, such as entrapment of one entity on or within the other, or of either or both entities on or within a third entity (e.g., a micelle).

The chaperon agent can be a naturally occurring substance, such as a protein (e.g., human serum albumin, low-density lipoprotein, or globulin), carbohydrate (e.g., a dextran, pullulan, chitin, chitosan, inulin, cyclodextrin or hyaluronic acid), or lipid. It can also be a recombinant or synthetic molecule, such as a synthetic polymer, e.g., a synthetic polyamino acid. Examples of polyamino acids include polylysine (PLL), poly L-aspartic acid, poly L-glutamic acid, styrene-maleic acid anhydride copolymer, poly(L-lactide-co-glycolied) copolymer, divinyl ether-maleic anhydride copolymer, N-(2-hydroxypropyl)methacrylamide copolymer (HMPA), polyethylene glycol (PEG), polyvinyl alcohol (PVA), polyurethane, poly(2-ethylacryllic acid), N-isopropylacrylamide polymers, and polyphosphazine.

In one example, the chaperon agent is a micelle, liposome, nanoparticle, or microsphere, in which the oligonucleotide/interfering RNA is encapsulated. Methods for preparing such a micelle, liposome, nanoparticle, or microsphere are well known in the art. See, e.g., U.S. Pat. Nos. 5,108,921; 5,354,844; 5,416,016; and 5,527,528.

In another example, the chaperon agent serves as a substrate for attachment of one or more of a fusogenic or condensing agent.

A fusogenic agent is responsive to the local pH. For instance, upon encountering the pH within an endosome, it can cause a physical change in its immediate environment, e.g., a change in osmotic properties which disrupts or increases the permeability of the endosome membrane, thereby facilitating release of the antisense oligonucleotide into host cell's cytoplasm. A preferred fusogenic agent changes charge, e.g., becomes protonated at a pH lower than a physiological range (e.g., at pH 4.5-6.5). Fusogenic agents can be molecules containing an amino group capable of undergoing a change of charge (e.g., protonation) when exposed to a specific pH range. Such fusogenic agents include polymers having polyamino chains (e.g., polyethyleneimine) and membrane disruptive agents (e.g., mellittin). Other examples include polyhistidine, polyimidazole, polypyridine, polypropyleneimine, and a polyacetal substance (e.g., a cationic polyacetal).

A condensing agent interacts with the antisense oligonucleotide, causing it to condense (e.g., reduce the size of the oligonucleotide), thus protecting it against degradation. Preferably, the condensing agent includes a moiety (e.g., a charged moiety) that interacts with the oligonucleotide via, e.g., ionic interactions. Examples of condensing agents include polylysine, spermine, spermidine, polyamine or quarternary salt thereof, pseudopeptide-polyamine, peptidomimetic polyamine, dendrimer polyamine, arginine, amidine, protamine, cationic lipid, cationic porphyrin, and alpha helical peptide.

Without further elaboration, it is believed that one skilled in the art can, based on the above description, utilize the present invention to its fullest extent. The following specific embodiments are, therefore, to be construed as merely illustrative, and not limitative of the remainder of the disclosure in any way whatsoever. All publications cited herein are incorporated by reference for the purposes or subject matter referenced herein.

Example 1

Preparation of Humanized Anti-IL-20 Antibodies

Exemplary humanized anti-IL-20 antibodies HL1 and HL2 were prepared as follows, using mouse monoclonal antibody 7E (mAb 7E) as the parent antibody. mAb 7E was described in U.S. Pat. Nos. 7,435,800 and 7,786,274, both of which are incorporated by reference herein. The amino acid sequences of the $V_H$ and $V_L$ chains of mAb 7E are shown below:

Amino Acid Sequence of mAb 7E $V_H$:

MYLGLNYVFIVFLLNGVQSELKLEESGG
GLVQPGGSMKLSCAASGFTFSDAWMDW
VRQSPEKGLEWIAEIRSKANNYATYFAE
SVKGRFTISRDDSKSGVYLQMNNLRAE
DTGIYFCTKLSLRYWFFDVWGAGTTVT
VSS (SEQ ID NO:9)

Amino Acid Sequence of mAb 7E $V_L$:

MMSPAQFLFLLVLWIRETNGDFVMTQT
PLTLSVTIGQPASISCKSSQSLLDSDGKT
YLNWLLQRPGQSPKHLIYLVSKLDSGV
PDRFTGSGSGTDFTLRISRVEAEDLGVY
YCWQSTHFPWTFGGGTKLEIK (SEQ ID NO:10)

The italic regions refer to the signal peptides in 7E $V_H$ and $V_L$.
Humanization of 7E $V_H$ Human $V_H$ sequences having framework regions (FRs) homologous to those of the mAb 7E $V_H$ chain were identified by searching the GenBank database using FRs of 7E $V_H$ as search queries. A sequence alignment between 7E $V_H$ and its predicted parental germline $V_H$ segment J606.4.82 (Johnston et al. 2006, *J. Immunol.* 176:4221-4234) is shown below:

```
                           1          2          3
               123456789 0123456789 0123456789 0123456789
    7E VH      ELKLEESGG GLVQPGGSMK LSCAASGFTF SDAWMDWVRQ
    J606.4.82  EVKLEESGG GLVQPGGSMK LSCAASGFTF SDAWMDWVRQ
                *

4          5             6          7
               0123456789 0122223456789 0123456789 0123456789
                                 abc
    7E VH      SPEKGLEWIA EIRSKANNYATYF AESVKGRFTI SRDDSKSGVY
    J606.4.82  SPEKGLEWVA EIRNKANNHATYY AESVKGRFTI SRDDSKSSVY
                        *    *   *   *                    *

1          1
                8             9              0          1
               0122223456789 0123456789 000123456789 0123
                  abc                        ab
    7E VH      LQMNNLRAEDTGI YFCTKLSLRY WFFDVWGAGTTV TVSS (SEQ ID NO: 11)
    J606.4.82  LQMNSLRAEDTGI YYCTR                        (SEQ ID NO: 12)
                   *           *  *
```

Positions of the residues indicated above were determined according to Kabat et al., 1991, "Sequences of Proteins of Immunological Interests," Fifth edition, NIH Publication No. 91-3242, U.S. Department of Health and Human Services. The CDR regions are underlined and numbered following Kabat et al. Asterisks indicate the differences between the 7E $V_H$ and the human parental germline $V_H$.

Human L06102 $V_H$ chain (Shaw et al. 1995, Ann. N.Y. Acad. Sci. 764:370-373) was chosen as an acceptor for humanization of the heavy chain. The CDR sequences of 7E $V_H$ were first transferred to the corresponding positions of L06102 $V_H$. Next, residues within the FRs of 7E $V_H$ at positions 48, 49, and 94 were retained in the humanized $V_H$. These residues were predicted to interact with the CDRs as determined by three-dimensional modeling analysis. The amino acid sequence of the resultant humanized $V_H$, Hu7E $V_H$, aligned with the sequences of 7E $V_H$ and L06102 $V_H$, is shown in below:

```
                         1           2           3
             123456789 0123456789  0123456789  0123456789
7E VH        ELKLEESGG GLVQPGGSMK  LSCAASGFTF  SDAWMDWVRQ
Hu7E VH      EVQLVESGG GLVQPGGSLK  LSCAASGFTF  SDAWMDWVRQ
L06102 VH    EVQLVESGG GLVQPGGSLK  LSCAASGFTF  S-----WVRQ 4            5              6           7
             0123456789  0122223456789  0123456789  0123456789
                              abc
7E VH        SPEKGLEWIA  EIRSKANNYATYF  AESVKGRFTI  SRDDSKSGVY
Hu7E VH      ASGKGLEWIA  EIRSKANNYATYF  AESVKGRFTI  SRDDSKNTAY
L06102 VH    ASGKGLEWVG  -------------  ------RFTI  SRDDSKNTAY 1           1
             8              9              0           1
             0122223456789  0123456789     000123456789 0123
                  abc                           ab
7E VH        LQMNNLRAEDTGI  YFCTKLSLRY     WFFDVWGAGTTV TVSS  (SEQ ID NO: 11)
Hu7E VH      LQMNSLKTEDTAV  YYCTKLSLRY     WFFDVWGQGTLV TVSS  (SEQ ID NO: 3)
L06102 VH    LQMNSLKTEDTAV  YYCTG-----     -----WGQGTLV TVSS  (SEQ ID NO: 13)
```

Again, positions of the residues in the $V_H$ chain are determined following Kabat et al. and the CDR regions are underlined. The CDRs in the L06102 $V_H$, which were replaced with those of the 7E $V_H$, are not shown in the alignment above. The FR residues noted above are also underlined.

Humanization of 7E $V_L$

Shown below is a sequence alignment between mAb 7E $V_L$ and its predicted parental germline V segment, bd2 (Schable et al. 1999, *Eur. J. Immunol.* 29: 2082-2086). Positions of the residues are determined following Kabat et al. The asterisks indicate differences between 7E $V_L$ and bd2 amino acid sequences.

```
                       1            2                 3
           123456789  0123456789   012345677777789   0123456789
                                         abcde
7E VL      DFVMTQTPL  TLSVTIGQPA   SISCKSSQSLLDSDG   KTYLNWLLQR
bd2        DVVMTQTPL  TLSVTIGQPA   SISCKSSQSLLDSDG   KTYLNWLLQR
            *

4           5           6           7
           0123456789  0123456789  0123456789  0123456789
7E VL      PGQSPKHLIY  LVSKLDSGVP  DRFTGSGSGT  DFTLRISRVE
bd2        PGQSPKRLIY  LVSKLDSGVP  DRFTGSGSGT  DFTLKISRVE
                 *                                  *

1
           8           9           0
           0123456789  0123456789  01234567
7E VL      AEDLGVYYCW  QSTHFPWTFG  GGTKLEIK  (SEQ ID NO: 14)
bd2        AEDLGVYYCW  QGTHFP               (SEQ ID NO: 16)
                        *
```

Based on the homology search using the 7E $V_L$ framework sequences as search queries, a human Vκ chain described in GenBank Accession Number BG758592 was chosen as an acceptor for humanization of the $V_L$ chain.

The CDR sequences of 7E $V_L$ were transferred to the corresponding positions of the BG758592 $V_L$ chain. Further, positions 2, 36 and 46 in the framework regions of 7E $V_L$ were retained in the humanized $V_L$. These positions were predicted to interact with CDRs as determined by the three-dimensional modeling analysis disclosed above. The amino acid sequence of the resultant humanized $V_L$, Hu7E $V_L$1, aligned with those of the 7E $V_L$ and BG758592 $V_L$, is shown below:

```
                        1          2             3
              123456789 0123456789 012345677777789 0123456789
                                       abcde
7E VL         DFVMTQTPL TLSVTIGQPA SISCKSSQSLLDSDG KTYLNWLLQR
Hu7E VL1      DFVMTQTPL SLSVTPGQPA SISCKSSQSLLDSDG KTYLNWLLQK
Hu7E VL2      DIVMTQTPL SLSVTPGQPA SISCKSSQSLLDSDG KTYLNWLLQK
BG758592 VL   DIVMTQTPL SLSVTPGQPA SISC----------- -----WYLQK 4          5          6          7
              0123456789 0123456789 0123456789 0123456789
7E VL         PGQSPKHLIY LVSKLDSGVP DRFTGSGSGT DFTLRISRVE
Hu7E VL1      PGQSPQHLIY LVSKLDSGVP DRFSGSGSGT DFTLKISRVE
Hu7E VL2      PGQSPQHLIY LVSKLDSGVP DRFSGSGSGT DFTLKISRVE
BG758592 VL   PGQSPQLLIY -------GVP DRFSGSGSGT DFTLKISRVE 1
              8          9       0
              0123456789 0123456789 01234567
7E VL         AEDLGVYYCW QSTHFPWTFG GGTKLEIK (SEQ ID NO: 14)
Hu7E VL1      AEDVGVYYCW QSTHFPWTFG GGTKVEIK (SEQ ID NO: 15)
Hu7E VL2      AEDVGVYYCW QSTHFPWTFG GGTKVEIK (SEQ ID NO: 7)
BG758592 VL   AEDVGVYYC- --------FG GGTKVEIK (SEQ ID NO: 17)
```

Numbers above the sequences indicate amino acid residue positions in VL as determined following Kabat et al. The CDR sequences and the residues within the FRs noted above are underlined in the 7E $V_L$. The CDR regions in BG758592 $V_L$ are omitted.

While a phenylalanine residue (F) at position 2 in mouse 7E $V_L$ is located at a framework position that was predicted to be important for the formation of the proper CDR structures, detailed molecular modeling analysis of the 7E variable regions suggested that an amino acid residue at position 2 in Hu7E VL1 could be replaced with the corresponding residue, isoleucine (I), in the human BG758592 $V_L$ without losing the antigen-binding affinity. In order to further reduce potential immunogenicity of humanized 7E antibody, a second humanized $V_L$ (Hu7E $V_L$2) was designed, in which a phenylalanine residue at position 2 in Hu7E $V_L$1 was replaced with an isoleucine residue. The amino acid sequence of Hu7E $V_L$2 is also shown in the alignment above.

Nucleotide sequences encoding the humanized Hu7E $V_H$ and Hu7E $V_L$1 and $V_L$2 were each cloned into an expression vector from Invivogen via the EcoRI and NheI cloning sites (for the $V_H$ gene) or the NcoI and BsiWI cloning sites (for the $V_L$1 and $V_L$2 genes). The resultant expression vectors were co-transfected into CHO cells following routine methods. The transfected CHO cells were cultured under suitable conditions allowing the expression of the Hu7E $V_H$ and Hu7E $V_L$1 chains (form humanized antibody HL1) or Hu7E $V_H$ and $V_L$2 chains (form humanized antibody HL2). The culture medium was then collected and the humanized anti-IL-20 antibodies contained therein were isolated by a protein A column.

Example 2

Biological Function Analysis of Humanized Anti-IL-20 Antibody

The antigen binding affinity of the humanized anti-IL-20 antibodies prepared in Example 1 above, as well as those of the parent antibody and a chimeric antibody derived therefrom, was examined via the standard BIOCORE technology following the manufacturer's protocol. The results are shown below:

| | |
|---|---|
| Parent antibody 7E: | $6.8 \times 10^{-10}$ |
| Humanized antibody HL1: | $3.6 \times 10^{-9}$ |
| Humanized antibody HL2: | $1.2 \times 10^{-9}$ |
| Chimeric antibody: | $4.2 \times 10^{-9}$ |

Unexpected, both humanized antibodies HL1 and HL2 showed antigen-binding affinities similar to that of the parent antibody. In particular, humanized antibody HL2 showed an antigen-binding affinity higher than the chimeric antibody.

The biological function of the humanized anti-IL-20 antibody noted above was analyzed via an inhibition of osteoclast differentiation assay. The parent mouse 7E antibody and a chimeric antibody derived therefrom were used as controls. The chimeric antibody was constructed by ligating the mAb 7E variable regions with the Fc region of a human IgG.

The osteoclast differentiation assay was performed as described in Hsu et al., *J Exp Med.* 2011, 208(9):1849-61. Briefly, bone marrow cells (BMCs) from the tibias of C57BL6 mice were incubated for 12 h (37° C./5% $CO_2$). Non-adherent cells were collected and seeded in 24-well plates ($2 \times 10^6$ cells per well) and cultured in the same medium supplemented with 30 ng/ml of recombinant murine macrophage colony-stimulating factor (M-CSF) (PeproTech). After 48 hours, M-CSF-derived osteoclast precursor cells were cultured with murine M-CSF (40 ng/ml) and sRANKL (100 ng/ml) (PeproTech) until the end of the experiment.

To analyze the effect of the 7E, chimeric, and humanized antibodies on osteoclast differentiation, BMCs were cultured for 12 h. Non-adherent cells were cultured in a-MEM containing MCSF to drive to OC precursors for 48 hours. One of the three anti-IL-20 antibodies, the 7E antibody, chimeric antibody, and humanized antibody (0.5 µg/ml) or a control hIgG (0.5 μg/ml) was added to the OC precursors. The cells were incubated with M-CSF (40 ng/ml) and sRANKL (100 ng/ml) for 6-8 days. To calculate the number of osteoclasts, the cells were fixed in acetone and stained for TRAP using an acid phosphatase kit (Sigma-Aldrich). TRAP-positive multi-nucleated cells containing three or more nuclei were considered as osteoclasts. As shown in the FIG. 1, the humanized antibody Hu HL2 (7E HL-2) unexpectedly exhibited the same effect as the parent mAb 7E in inhibiting OC differentiation. The humanized antibody inhibited 50% of OC differentiation at the concentration of 0.5 ug/ml. These results demonstrate that, like the parent mouse antibody, the humanized anti-IL-20 antibody can be used as a therapeutic agent in alleviating bone loss, e.g., bone loss associated with post-menopause osteoporosis, rheumatoid arthritis, cancer-induced osteolysis.

Other Embodiments

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the claims.

What is claimed is:

1. An isolated humanized antibody, comprising:
    a heavy chain variable region ($V_H$), which comprises an amino acid sequence that is (i) identical to SEQ ID NO:1 or SEQ ID NO:3, or (ii) at least 90% identical to SEQ ID NO:1 or SEQ ID NO:3, and consisting of one or more mutations in one or more framework regions (FRs) in SEQ ID NO:1 or SEQ ID NO:3, and
    a light chain variable region ($V_L$), which comprises an amino acid sequence that is (i) identical to SEQ ID NO:5 or SEQ ID NO:7, or (ii) at least 90% identical to SEQ ID NO:5 or SEQ ID NO:7, and consisting of one or more mutations in one or more FRs in SEQ ID NO:5 or SEQ ID NO:7;
    wherein the antibody binds to human interleukin 20 (IL-20).

2. The isolated antibody of claim 1, wherein the $V_H$ comprises an amino acid sequence at least 95% identical to SEQ ID NO:1 or SEQ ID NO:3, and the $V_L$ comprises an amino acid sequence at least 95% identical to SEQ ID NO:5 or SEQ ID NO:7.

3. The isolated antibody of claim 2, wherein the $V_H$ comprises the amino acid sequence of SEQ ID NO:1 or SEQ ID NO:3, and the $V_L$ comprises the amino acid sequence of SEQ ID NO:5 or SEQ ID NO:7.

4. The isolated antibody of claim 1, wherein the antibody is a full-length antibody.

5. The isolated antibody of claim 4, wherein the full-length antibody is an IgG molecule.

6. The isolated antibody of claim 1, wherein the antibody is an antigen-binding fragment.

7. The isolate antibody of claim 6, wherein the antigen-binding fragment is Fab.

8. A pharmaceutical composition, comprising the isolated antibody of claim 1 and a pharmaceutically acceptable carrier.

9. A method for treating a disease associated with an upregulated IL-20-mediated signaling pathway, comprising administering to a patient in need thereof an effective amount of the antibody of claim 1.

10. The method of claim 9, wherein the disease associated with the IL-20-mediated signaling pathway is osteoporosis or rheumatoid arthritis.

11. The method of claim 10, wherein the disease associated with the IL-20-mediated signaling pathway is osteoporosis.

12. The method of claim 11, wherein the osteoporosis is caused by an inflammatory disease, estrogen deficiency, androgen deficiency, or cancer-induced osteolysis.

13. The isolated antibody of claim 1, wherein the one or more mutations in both the $V_H$ and $V_L$ are conservative substitutions.

14. The isolated antibody of claim 1, wherein the $V_H$ retains the amino acid residues at positions 48, 49, and 94 in SEQ ID NO:3 and the $V_L$ retains the amino acid residues at positions 2, 36, and 46 in SEQ ID NO:7.

15. The isolated antibody of claim 1, wherein the $V_H$ comprises the amino acid sequence of SEQ ID NO:1 or SEQ ID NO:3, and the $V_L$ comprises the amino acid sequence of SEQ ID NO:15.

* * * * *

SEQUENCE LISTING

<160> NUMBER OF SEQ ID NOS: 17

<210> SEQ ID NO 1
<211> LENGTH: 140
<212> TYPE: PRT
<213> ORGANISM: Artificial sequence
<220> FEATURE:
<223> OTHER INFORMATION: precursor VH chain variable region of exemplary
      humanized anti-IL-20 antibodies HL1 and HL2

<400> SEQUENCE: 1

Met Tyr Leu Gly Leu Asn Tyr Val Phe Ile Val Phe Leu Leu Asn Gly
1               5                   10                  15

Val Gln Ser Glu Val Gln Leu Val Glu Ser Gly Gly Gly Leu Val Gln
            20                  25                  30

Pro Gly Gly Ser Leu Lys Leu Ser Cys Ala Ala Ser Gly Phe Thr Phe
        35                  40                  45

Ser Asp Ala Trp Met Asp Trp Val Arg Gln Ala Ser Gly Lys Gly Leu
    50                  55                  60

Glu Trp Ile Ala Glu Ile Arg Ser Lys Ala Asn Asn Tyr Ala Thr Tyr
65                  70                  75                  80

Phe Ala Glu Ser Val Lys Gly Arg Phe Thr Ile Ser Arg Asp Asp Ser
                85                  90                  95

Lys Asn Thr Ala Tyr Leu Gln Met Asn Ser Leu Lys Thr Glu Asp Thr
            100                 105                 110

Ala Val Tyr Tyr Cys Thr Lys Leu Ser Leu Arg Tyr Trp Phe Phe Asp
        115                 120                 125

Val Trp Gly Gln Gly Thr Leu Val Thr Val Ser Ser
    130                 135                 140

<210> SEQ ID NO 2
<211> LENGTH: 420
<212> TYPE: DNA
<213> ORGANISM: Artificial sequence
<220> FEATURE:
<223> OTHER INFORMATION: nucleotide sequence encoding the amino acid
      sequence of the precursor VH chain variable region of exemplary
      humanized anti-IL-20 antibodies HL1 and HL2

<400> SEQUENCE: 2
atgtacttgg gactgaacta tgttttcatc gtttttctcc tgaatggtgt ccagagtgaa      60
gtgcagcttg tggagtctgg aggaggcttg gtgcagcctg gaggatccct gaaactctct     120
tgtgctgcct ctggattcac ttttagtgac gcctggatgg actgggtccg ccaggcttcc     180

```
gggaaggggc ttgagtggat tgctgaaatt agaagcaaag ctaataatta tgcaacatac      240
tttgctgagt ctgtgaaagg gaggttcacc atctcaagag atgattccaa aaacaccgcc      300
tacctgcaaa tgaacagctt aaaaaccgag acactgccg tttattactg taccaagtta       360
tcactgcgtt actggttctt cgatgtctgg ggccagggga ccctggtcac cgtctcctca      420
```

<210> SEQ ID NO 3
<211> LENGTH: 121
<212> TYPE: PRT
<213> ORGANISM: Artificial sequence
<220> FEATURE:
<223> OTHER INFORMATION: mature VH chain variable region (which lacks
      the signal peptide) of the exemplary humanized anti-IL-20
      antibodies HL1 and HL2

<400> SEQUENCE: 3

```
Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Ser Asp Ala
            20                  25                  30

Trp Met Asp Trp Val Arg Gln Ala Ser Gly Lys Gly Leu Glu Trp Ile
        35                  40                  45

Ala Glu Ile Arg Ser Lys Ala Asn Asn Tyr Ala Thr Tyr Phe Ala Glu
    50                  55                  60

Ser Val Lys Gly Arg Phe Thr Ile Ser Arg Asp Asp Ser Lys Asn Thr
65                  70                  75                  80

Ala Tyr Leu Gln Met Asn Ser Leu Lys Thr Glu Asp Thr Ala Val Tyr
                85                  90                  95

Tyr Cys Thr Lys Leu Ser Leu Arg Tyr Trp Phe Phe Asp Val Trp Gly
            100                 105                 110

Gln Gly Thr Leu Val Thr Val Ser Ser
        115                 120
```

<210> SEQ ID NO 4
<211> LENGTH: 363
<212> TYPE: DNA
<213> ORGANISM: Artificial sequence
<220> FEATURE:
<223> OTHER INFORMATION: nucleotide sequence encoding the amino acid
      sequence of the mature VH chain variable region (which lacks the
      signal peptide) of the exemplary humanized anti-IL-20 antibodies
      HL1 and HL2

<400> SEQUENCE: 4

```
gaagtgcagc ttgtggagtc tggaggaggc ttggtgcagc ctggaggatc cctgaaactc      60
tcttgtgctg cctctggatt cacttttagt gacgcctgga tggactgggt ccgccaggct      120
tccgggaagg ggcttgagtg gattgctgaa attagaagca agctaataa ttatgcaaca       180 tactttgctg agtctgtgaa agggaggttc accatctcaa gagatgattc aaaaacacc       240 gcctacctgc aaatgaacag cttaaaaacc gaggacactg ccgtttatta ctgtaccaag      300
ttatcactgc gttactggtt cttcgatgtc tggggccagg gaccctggt caccgtctcc       360 tca                                                                    363
```

<210> SEQ ID NO 5
<211> LENGTH: 132
<212> TYPE: PRT
<213> ORGANISM: Artificial sequence
<220> FEATURE:
<223> OTHER INFORMATION: precursor VL chain variable region of exemplary
      humanized anti-IL-20 antibody HL2

<400> SEQUENCE: 5

```
Met Met Ser Pro Ala Gln Phe Leu Phe Leu Val Leu Trp Ile Arg
1               5                   10                  15

Glu Thr Asn Gly Asp Ile Val Met Thr Gln Thr Pro Leu Ser Leu Ser
                20                  25                  30

Val Thr Pro Gly Gln Pro Ala Ser Ile Ser Cys Lys Ser Gln Ser
            35                  40                  45

Leu Leu Asp Ser Asp Gly Lys Thr Tyr Leu Asn Trp Leu Leu Gln Lys
        50                  55                  60

Pro Gly Gln Ser Pro Gln His Leu Ile Tyr Leu Val Ser Lys Leu Asp
65                  70                  75                  80

Ser Gly Val Pro Asp Arg Phe Ser Gly Ser Gly Ser Gly Thr Asp Phe
                85                  90                  95

Thr Leu Lys Ile Ser Arg Val Glu Ala Glu Asp Val Gly Val Tyr Tyr
            100                 105                 110

Cys Trp Gln Ser Thr His Phe Pro Trp Thr Phe Gly Gly Gly Thr Lys
            115                 120                 125

Val Glu Ile Lys
    130
```

<210> SEQ ID NO 6
<211> LENGTH: 396
<212> TYPE: DNA
<213> ORGANISM: Artificial sequence
<220> FEATURE:
<223> OTHER INFORMATION: nucleotide sequence encoding the amino acid
    sequence of the precursor VL chain variable region of exemplary
    humanized anti-IL-20 antibody HL2

<400> SEQUENCE: 6

```
atgatgagtc ctgcccagtt cctgtttctg ttggtgctct ggattcggga aaccaacggt      60
gatatcgtga tgacccagac tccactctct ttgtccgtta cccctggaca accagcctcc     120
atctcttgca agtcaagtca gagcctcttg gatagtgatg gaaagacata tttgaattgg     180
ttgttacaga agccaggcca gtctccacag cacctcatct atctggtgtc taaactggac     240
tctggagtcc ctgacaggtt cagtggcagt ggatcaggga ccgatttcac actgaaaatc     300
agcagagtgg aggctgagga tgttggagtt tattattgct ggcaaagtac acattttccc     360
tggaccttcg gtggaggcac caaggtggaa atcaaa                               396
```

<210> SEQ ID NO 7
<211> LENGTH: 112
<212> TYPE: PRT
<213> ORGANISM: Artificial sequence
<220> FEATURE:
<223> OTHER INFORMATION: mature VL chain variable region (which lacks
    the signal peptide) of exemplary humanized anti-IL-20 antibody HL2

<400> SEQUENCE: 7

```
Asp Ile Val Met Thr Gln Thr Pro Leu Ser Leu Ser Val Thr Pro Gly
1               5                   10                  15

Gln Pro Ala Ser Ile Ser Cys Lys Ser Gln Ser Leu Leu Asp Ser
            20                  25                  30

Asp Gly Lys Thr Tyr Leu Asn Trp Leu Leu Gln Lys Pro Gly Gln Ser
        35                  40                  45

Pro Gln His Leu Ile Tyr Leu Val Ser Lys Leu Asp Ser Gly Val Pro
    50                  55                  60

Asp Arg Phe Ser Gly Ser Gly Ser Gly Thr Asp Phe Thr Leu Lys Ile
```

```
                65                  70                  75                  80
Ser Arg Val Glu Ala Glu Asp Val Gly Val Tyr Tyr Cys Trp Gln Ser
                    85                  90                  95

Thr His Phe Pro Trp Thr Phe Gly Gly Gly Thr Lys Val Glu Ile Lys
                    100                 105                 110
```

<210> SEQ ID NO 8
<211> LENGTH: 336
<212> TYPE: DNA
<213> ORGANISM: Artificial sequence
<220> FEATURE:
<223> OTHER INFORMATION: nucleotide sequence encoding the amino acid
      sequence of mature VL chain variable region (which lacks the
      signal peptide) of exemplary humanized anti-IL-20 antibody HL2

<400> SEQUENCE: 8

```
gatatcgtga tgacccagac tccactctct ttgtccgtta cccctggaca accagcctcc        60
atctcttgca agtcaagtca gagcctcttg gatagtgatg gaaagacata tttgaattgg       120
ttgttacaga agccaggcca gtctccacag cacctcatct atctggtgtc taaactggac       180
tctggagtcc ctgacaggtt cagtggcagt ggatcaggga ccgatttcac actgaaaatc       240
agcagagtgg aggctgagga tgttggagtt tattattgct ggcaaagtac acattttccc       300
tggaccttcg gtggaggcac caaggtggaa atcaaa                                 336
```

<210> SEQ ID NO 9
<211> LENGTH: 140
<212> TYPE: PRT
<213> ORGANISM: Artificial sequence
<220> FEATURE:
<223> OTHER INFORMATION: precursor VH chain variable region of
      monoclonal antibody 7E

<400> SEQUENCE: 9

```
Met Tyr Leu Gly Leu Asn Tyr Val Phe Ile Val Phe Leu Leu Asn Gly
1               5                   10                  15

Val Gln Ser Glu Leu Lys Leu Glu Glu Ser Gly Gly Gly Leu Val Gln
                20                  25                  30

Pro Gly Gly Ser Met Lys Leu Ser Cys Ala Ala Ser Gly Phe Thr Phe
            35                  40                  45

Ser Asp Ala Trp Met Asp Trp Val Arg Gln Ser Pro Glu Lys Gly Leu
    50                  55                  60

Glu Trp Ile Ala Glu Ile Arg Ser Lys Ala Asn Asn Tyr Ala Thr Tyr
65                  70                  75                  80

Phe Ala Glu Ser Val Lys Gly Arg Phe Thr Ile Ser Arg Asp Asp Ser
                85                  90                  95

Lys Ser Gly Val Tyr Leu Gln Met Asn Asn Leu Arg Ala Glu Asp Thr
                100                 105                 110

Gly Ile Tyr Phe Cys Thr Lys Leu Ser Leu Arg Tyr Trp Phe Phe Asp
            115                 120                 125

Val Trp Gly Ala Gly Thr Thr Val Thr Val Ser Ser
    130                 135                 140
```

<210> SEQ ID NO 10
<211> LENGTH: 132
<212> TYPE: PRT
<213> ORGANISM: Artificial sequence
<220> FEATURE:
<223> OTHER INFORMATION: the precursor VL chain variable region of
      monoclonal antibody 7E

<400> SEQUENCE: 10

```
Met Met Ser Pro Ala Gln Phe Leu Phe Leu Leu Val Leu Trp Ile Arg
1               5                   10                  15

Glu Thr Asn Gly Asp Phe Val Met Thr Gln Thr Pro Leu Thr Leu Ser
                20                  25                  30

Val Thr Ile Gly Gln Pro Ala Ser Ile Ser Cys Lys Ser Gln Ser
            35                  40                  45

Leu Leu Asp Ser Asp Gly Lys Thr Tyr Leu Asn Trp Leu Leu Gln Arg
        50                  55                  60

Pro Gly Gln Ser Pro Lys His Leu Ile Tyr Leu Val Ser Lys Leu Asp
65                  70                  75                  80

Ser Gly Val Pro Asp Arg Phe Thr Gly Ser Gly Ser Gly Thr Asp Phe
                85                  90                  95

Thr Leu Arg Ile Ser Arg Val Glu Ala Glu Asp Leu Gly Val Tyr Tyr
                100                 105                 110

Cys Trp Gln Ser Thr His Phe Pro Trp Thr Phe Gly Gly Gly Thr Lys
            115                 120                 125

Leu Glu Ile Lys
        130

<210> SEQ ID NO 11
<211> LENGTH: 121
<212> TYPE: PRT
<213> ORGANISM: Artificial sequence
<220> FEATURE:
<223> OTHER INFORMATION: the mature VH chain variable region (which
      lacks the signal peptide) of monoclonal antibody 7E

<400> SEQUENCE: 11

Glu Leu Lys Leu Glu Glu Ser Gly Gly Gly Leu Val Gln Pro Gly Gly
1               5                   10                  15

Ser Met Lys Leu Ser Cys Ala Ala Ser Gly Phe Thr Phe Ser Asp Ala
                20                  25                  30

Trp Met Asp Trp Val Arg Gln Ser Pro Glu Lys Gly Leu Glu Trp Ile
            35                  40                  45

Ala Glu Ile Arg Ser Lys Ala Asn Asn Tyr Ala Thr Tyr Phe Ala Glu
        50                  55                  60

Ser Val Lys Gly Arg Phe Thr Ile Ser Arg Asp Asp Ser Lys Ser Gly
65                  70                  75                  80

Val Tyr Leu Gln Met Asn Asn Leu Arg Ala Glu Asp Thr Gly Ile Tyr
                85                  90                  95

Phe Cys Thr Lys Leu Ser Leu Arg Tyr Trp Phe Phe Asp Val Trp Gly
                100                 105                 110

Ala Gly Thr Thr Val Thr Val Ser Ser
        115                 120

<210> SEQ ID NO 12
<211> LENGTH: 100
<212> TYPE: PRT
<213> ORGANISM: Artificial sequence
<220> FEATURE:
<223> OTHER INFORMATION: human germline antibody VH segment J606.4.82

<400> SEQUENCE: 12

Glu Val Lys Leu Glu Ser Gly Gly Gly Leu Val Gln Pro Gly Gly
1               5                   10                  15

Ser Met Lys Leu Ser Cys Ala Ala Ser Gly Phe Thr Phe Ser Asp Ala
                20                  25                  30

Trp Met Asp Trp Val Arg Gln Ser Pro Glu Lys Gly Leu Glu Trp Val
```

```
                35                  40                  45
Ala Glu Ile Arg Asn Lys Ala Asn Asn His Ala Thr Tyr Tyr Ala Glu
 50                  55                  60

Ser Val Lys Gly Arg Phe Thr Ile Ser Arg Asp Asp Ser Lys Ser Ser
 65                  70                  75                  80

Val Tyr Leu Gln Met Asn Ser Leu Arg Ala Glu Asp Thr Gly Ile Tyr
                 85                  90                  95

Tyr Cys Thr Arg
            100

<210> SEQ ID NO 13
<211> LENGTH: 87
<212> TYPE: PRT
<213> ORGANISM: Artificial sequence
<220> FEATURE:
<223> OTHER INFORMATION: framework regions in human antibody L06102 VH
      chain (mature form)

<400> SEQUENCE: 13

Glu Val Gln Leu Val Glu Ser Gly Gly Gly Leu Val Gln Pro Gly Gly
 1               5                  10                  15

Ser Leu Lys Leu Ser Cys Ala Ala Ser Gly Phe Thr Phe Ser Trp Val
             20                  25                  30

Arg Gln Ala Ser Gly Lys Gly Leu Glu Trp Val Gly Arg Phe Thr Ile
         35                  40                  45

Ser Arg Asp Asp Ser Lys Asn Thr Ala Tyr Leu Gln Met Asn Ser Leu
 50                  55                  60

Lys Thr Glu Asp Thr Ala Val Tyr Tyr Cys Thr Gly Trp Gly Gln Gly
 65                  70                  75                  80

Thr Leu Val Thr Val Ser Ser
             85

<210> SEQ ID NO 14
<211> LENGTH: 112
<212> TYPE: PRT
<213> ORGANISM: Artificial sequence
<220> FEATURE:
<223> OTHER INFORMATION: mature VL chain variable region (which lacks
      the signal peptide) of monoclonal antibody 7E

<400> SEQUENCE: 14

Asp Phe Val Met Thr Gln Thr Pro Leu Thr Leu Ser Val Thr Ile Gly
 1               5                  10                  15

Gln Pro Ala Ser Ile Ser Cys Lys Ser Ser Gln Ser Leu Leu Asp Ser
             20                  25                  30

Asp Gly Lys Thr Tyr Leu Asn Trp Leu Leu Gln Arg Pro Gly Gln Ser
         35                  40                  45

Pro Lys His Leu Ile Tyr Leu Val Ser Lys Leu Asp Ser Gly Val Pro
 50                  55                  60

Asp Arg Phe Thr Gly Ser Gly Ser Gly Thr Asp Phe Thr Leu Arg Ile
 65                  70                  75                  80

Ser Arg Val Glu Ala Glu Asp Leu Gly Val Tyr Tyr Cys Trp Gln Ser
             85                  90                  95

Thr His Phe Pro Trp Thr Phe Gly Gly Gly Thr Lys Leu Glu Ile Lys
            100                 105                 110

<210> SEQ ID NO 15
<211> LENGTH: 112
<212> TYPE: PRT
<213> ORGANISM: Artificial sequence
```

-continued

<220> FEATURE:
<223> OTHER INFORMATION: mature VL chain variable region (which lacks
      the signal peptide) of exemplary humanized anti-IL-20 antibody HL1

<400> SEQUENCE: 15

Asp Phe Val Met Thr Gln Thr Pro Leu Ser Leu Ser Val Thr Pro Gly
1               5                   10                  15

Gln Pro Ala Ser Ile Ser Cys Lys Ser Ser Gln Ser Leu Leu Asp Ser
            20                  25                  30

Asp Gly Lys Thr Tyr Leu Asn Trp Leu Leu Gln Lys Pro Gly Gln Ser
        35                  40                  45

Pro Gln His Leu Ile Tyr Leu Val Ser Lys Leu Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Trp Gln Ser
                85                  90                  95

Thr His Phe Pro Trp Thr Phe Gly Gly Gly Thr Lys Val Glu Ile Lys
            100                 105                 110

<210> SEQ ID NO 16
<211> LENGTH: 100
<212> TYPE: PRT
<213> ORGANISM: Artificial sequence
<220> FEATURE:
<223> OTHER INFORMATION: human germline antibody bd2 VL segment

<400> SEQUENCE: 16

Asp Val Val Met Thr Gln Thr Pro Leu Thr Leu Ser Val Thr Ile Gly
1               5                   10                  15

Gln Pro Ala Ser Ile Ser Cys Lys Ser Ser Gln Ser Leu Leu Asp Ser
            20                  25                  30

Asp Gly Lys Thr Tyr Leu Asn Trp Leu Leu Gln Arg Pro Gly Gln Ser
        35                  40                  45

Pro Lys Arg Leu Ile Tyr Leu Val Ser Lys Leu Asp Ser Gly Val Pro
    50                  55                  60

Asp Arg Phe Thr Gly Ser Gly Ser Gly Thr Asp Phe Thr Leu Lys Ile
65                  70                  75                  80

Ser Arg Val Glu Ala Glu Asp Leu Gly Val Tyr Tyr Cys Trp Gln Gly
                85                  90                  95

Thr His Phe Pro
            100

<210> SEQ ID NO 17
<211> LENGTH: 80
<212> TYPE: PRT
<213> ORGANISM: Artificial sequence
<220> FEATURE:
<223> OTHER INFORMATION: framework regions in human antibody BG758592 VL
      chain (mature form)

<400> SEQUENCE: 17

Asp Ile Val Met Thr Gln Thr Pro Leu Ser Leu Ser Val Thr Pro Gly
1               5                   10                  15

Gln Pro Ala Ser Ile Ser Cys Trp Tyr Leu Gln Lys Pro Gly Gln Ser
            20                  25                  30

Pro Gln Leu Leu Ile Tyr Gly Val Pro Asp Arg Phe Ser Gly Ser Gly
        35                  40                  45

```
Ser Gly Thr Asp Phe Thr Leu Lys Ile Ser Arg Val Glu Ala Glu Asp
    50                  55                  60
Val Gly Val Tyr Tyr Cys Phe Gly Gly Gly Thr Lys Val Glu Ile Lys
65                  70                  75                  80
```